US007648725B2

(12) United States Patent
Van Sciver et al.

(10) Patent No.: US 7,648,725 B2
(45) Date of Patent: Jan. 19, 2010

(54) CLAMP MANDREL FIXTURE AND A METHOD OF USING THE SAME TO MINIMIZE COATING DEFECTS

(75) Inventors: Jason Van Sciver, Los Gatos, CA (US); Manish Gada, Santa Clara, CA (US); Jessie Madriaga, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 606 days.

(21) Appl. No.: 11/437,589

(22) Filed: May 19, 2006

(65) Prior Publication Data

US 2006/0210702 A1 Sep. 21, 2006

Related U.S. Application Data

(62) Division of application No. 10/319,042, filed on Dec. 12, 2002, now Pat. No. 7,074,276.

(51) Int. Cl.
*A61L 33/00* (2006.01)

(52) U.S. Cl. ...................... 427/2.1; 427/2.24; 427/2.28; 427/336; 427/426; 427/430.1

(58) Field of Classification Search ................ 427/2.24, 427/2.28, 336, 426, 430.1
See application file for complete search history.

(56) References Cited

U.S. PATENT DOCUMENTS

| | | | | |
|---|---|---|---|---|
| 1,133,334 | A * | 3/1915 | Strycker ........................ 269/6 | |
| 1,346,584 | A | 7/1920 | Angle | |
| 2,072,303 | A | 3/1937 | Hermann et al. | |
| 2,386,454 | A | 10/1945 | Frosch et al. | |
| 2,845,346 | A | 7/1958 | Scanlon et al. | |
| 3,016,875 | A | 1/1962 | Ballentine, Jr. et al. | |
| 3,226,245 | A | 12/1965 | Dettling et al. | |
| 3,773,737 | A | 11/1973 | Goodman et al. | |
| 3,827,139 | A | 8/1974 | Norteman | |
| 3,849,514 | A | 11/1974 | Gray, Jr. et al. | |
| 3,882,816 | A | 5/1975 | Rooz et al. | |
| 3,995,075 | A | 11/1976 | Cernauskas et al. | |
| 4,011,388 | A | 3/1977 | Murphy et al. | |
| 4,082,212 | A | 4/1978 | Headrick et al. | |
| 4,201,149 | A | 5/1980 | Koester et al. | |
| 4,226,243 | A | 10/1980 | Shalaby et al. | |

(Continued)

FOREIGN PATENT DOCUMENTS

DE 42 24 401 1/1994

(Continued)

OTHER PUBLICATIONS

U.S. Appl. No. 09/894,293, filed Jun. 27, 2001, Roorda et al.

(Continued)

*Primary Examiner*—Michael Barr
*Assistant Examiner*—Andrew Bowman
(74) *Attorney, Agent, or Firm*—Squire, Sanders & Dempsey, L.L.P.

(57) ABSTRACT

A mounting assembly for supporting a stent and a method of using the same to coat a stent is disclosed.

34 Claims, 5 Drawing Sheets

U.S. PATENT DOCUMENTS

| | | | | |
|---|---|---|---|---|
| 4,269,713 | A | 5/1981 | Yamashita et al. | |
| 4,290,383 | A | 9/1981 | Pfender | |
| 4,329,383 | A | 5/1982 | Joh | |
| 4,343,931 | A | 8/1982 | Barrows | |
| 4,459,252 | A | 7/1984 | MacGregor | |
| 4,489,670 | A | 12/1984 | Mosser et al. | |
| 4,529,792 | A | 7/1985 | Barrows | |
| 4,560,374 | A | 12/1985 | Hammerslag | |
| 4,611,051 | A | 9/1986 | Hayes et al. | |
| 4,616,593 | A | 10/1986 | Kawamura et al. | |
| 4,629,563 | A | 12/1986 | Wrasidlo | |
| 4,640,846 | A | 2/1987 | Kuo | |
| 4,656,242 | A | 4/1987 | Swan et al. | |
| 4,733,665 | A | 3/1988 | Palmaz | |
| 4,762,128 | A | 8/1988 | Rosenbluth | |
| 4,798,585 | A | 1/1989 | Inoue et al. | |
| 4,800,882 | A | 1/1989 | Gianturco | |
| 4,822,535 | A | 4/1989 | Ekman et al. | |
| 4,839,055 | A | 6/1989 | Ishizaki et al. | |
| 4,846,791 | A | 7/1989 | Hattler et al. | |
| 4,865,879 | A | 9/1989 | Finlay | |
| 4,882,168 | A | 11/1989 | Casey et al. | |
| 4,886,062 | A | 12/1989 | Wiktor | |
| 4,893,623 | A | 1/1990 | Rosenbluth | |
| 4,906,423 | A | 3/1990 | Frisch | |
| 4,931,287 | A | 6/1990 | Bae et al. | |
| 4,941,870 | A | 7/1990 | Okada et al. | |
| 4,955,899 | A | 9/1990 | Della Corna et al. | |
| 4,976,736 | A | 12/1990 | White et al. | |
| 4,977,901 | A | 12/1990 | Ofstead | |
| 4,992,312 | A | 2/1991 | Frisch | |
| 5,017,420 | A | 5/1991 | Marikar | |
| 5,019,096 | A | 5/1991 | Fox, Jr. et al. | |
| 5,033,405 | A | 7/1991 | Yamada et al. | |
| 5,037,392 | A | 8/1991 | Hillstead | |
| 5,037,427 | A | 8/1991 | Harada et al. | |
| 5,059,211 | A | 10/1991 | Stack et al. | |
| 5,095,848 | A | 3/1992 | Ikeno | |
| 5,100,992 | A | 3/1992 | Cohn et al. | |
| 5,112,457 | A | 5/1992 | Marchant | |
| 5,133,742 | A | 7/1992 | Pinchuk | |
| 5,163,952 | A | 11/1992 | Froix | |
| 5,165,919 | A | 11/1992 | Sasaki et al. | |
| 5,171,445 | A | 12/1992 | Zepf | |
| 5,188,734 | A | 2/1993 | Zepf | |
| 5,201,314 | A | 4/1993 | Bosley et al. | |
| 5,219,980 | A | 6/1993 | Swidler | |
| 5,229,045 | A | 7/1993 | Soldani | |
| 5,234,457 | A | 8/1993 | Andersen | |
| 5,242,399 | A | 9/1993 | Lau et al. | |
| 5,258,020 | A | 11/1993 | Froix | |
| 5,264,246 | A | 11/1993 | Ikeno | |
| 5,272,012 | A | 12/1993 | Opolski | |
| 5,292,516 | A | 3/1994 | Viegas et al. | |
| 5,298,260 | A | 3/1994 | Viegas et al. | |
| 5,300,295 | A | 4/1994 | Viegas et al. | |
| 5,306,286 | A | 4/1994 | Stack et al. | |
| 5,306,501 | A | 4/1994 | Viegas et al. | |
| 5,306,786 | A | 4/1994 | Moens et al. | |
| 5,308,338 | A | 5/1994 | Helfrich | |
| 5,328,471 | A | 7/1994 | Slepian | |
| 5,330,768 | A | 7/1994 | Park et al. | |
| 5,342,621 | A | 8/1994 | Eury | |
| 5,358,740 | A | 10/1994 | Bornside et al. | |
| 5,370,684 | A | 12/1994 | Vallana et al. | |
| 5,378,511 | A | 1/1995 | Cardinali et al. | |
| 5,380,299 | A | 1/1995 | Fearnot et al. | |
| 5,417,981 | A | 5/1995 | Endo et al. | |
| 5,421,955 | A | 6/1995 | Lau et al. | |
| 5,443,496 | A | 8/1995 | Schwartz et al. | |
| 5,447,724 | A | 9/1995 | Helmus et al. | |
| 5,455,040 | A | 10/1995 | Marchant | |
| 5,458,683 | A | 10/1995 | Taylor et al. | |
| 5,462,990 | A | 10/1995 | Hubbell et al. | |
| 5,464,650 | A | 11/1995 | Berg et al. | |
| 5,485,496 | A | 1/1996 | Lee et al. | |
| 5,514,154 | A | 5/1996 | Lau et al. | |
| 5,516,560 | A | 5/1996 | Harayama et al. | |
| 5,516,881 | A | 5/1996 | Lee et al. | |
| 5,527,337 | A | 6/1996 | Stack et al. | |
| 5,537,729 | A | 7/1996 | Kolobow | |
| 5,538,493 | A | 7/1996 | Gerken et al. | |
| 5,558,900 | A | 9/1996 | Fan et al. | |
| 5,569,295 | A | 10/1996 | Lam | |
| 5,569,463 | A | 10/1996 | Helmus et al. | |
| 5,578,048 | A | 11/1996 | Pasqualucci et al. | |
| 5,578,073 | A | 11/1996 | Haimovich et al. | |
| 5,584,877 | A | 12/1996 | Miyake et al. | |
| 5,603,721 | A | 2/1997 | Lau et al. | |
| 5,605,696 | A | 2/1997 | Eury et al. | |
| 5,607,442 | A | 3/1997 | Fischell et al. | |
| 5,607,467 | A | 3/1997 | Froix | |
| 5,609,629 | A | 3/1997 | Fearnot et al. | |
| 5,610,241 | A | 3/1997 | Lee et al. | |
| 5,611,775 | A | 3/1997 | Machold et al. | |
| 5,616,338 | A | 4/1997 | Fox, Jr. et al. | |
| 5,624,411 | A | 4/1997 | Tuch | |
| 5,628,730 | A | 5/1997 | Shapland et al. | |
| 5,628,786 | A | 5/1997 | Banas et al. | |
| 5,637,113 | A | 6/1997 | Tartaglia et al. | |
| 5,643,580 | A | 7/1997 | Subramaniam | |
| 5,644,020 | A | 7/1997 | Timmermann et al. | |
| 5,649,977 | A | 7/1997 | Campbell | |
| 5,656,082 | A | 8/1997 | Takatsuki et al. | |
| 5,658,995 | A | 8/1997 | Kohn et al. | |
| 5,667,767 | A | 9/1997 | Greff et al. | |
| 5,670,558 | A | 9/1997 | Onishi et al. | |
| 5,674,242 | A | 10/1997 | Phan et al. | |
| 5,679,400 | A | 10/1997 | Tuch | |
| 5,687,906 | A | 11/1997 | Nakagawa | |
| 5,700,286 | A | 12/1997 | Tartaglia et al. | |
| 5,702,754 | A | 12/1997 | Zhong | |
| 5,707,385 | A | 1/1998 | Williams | |
| 5,711,958 | A | 1/1998 | Cohn et al. | |
| 5,713,949 | A | 2/1998 | Jayaraman | |
| 5,716,981 | A * | 2/1998 | Hunter et al. | 514/449 |
| 5,721,131 | A | 2/1998 | Rudolph et al. | |
| 5,723,219 | A | 3/1998 | Kolluri et al. | |
| 5,735,897 | A | 4/1998 | Buirge | |
| 5,741,554 | A | 4/1998 | Tisone | |
| 5,746,998 | A | 5/1998 | Torchilin et al. | |
| 5,756,553 | A | 5/1998 | Iguchi et al. | |
| 5,759,205 | A | 6/1998 | Valentini | |
| 5,766,710 | A | 6/1998 | Turnlund et al. | |
| 5,769,883 | A | 6/1998 | Buscemi et al. | |
| 5,772,864 | A | 6/1998 | Møller et al. | |
| 5,776,184 | A | 7/1998 | Tuch | |
| 5,783,657 | A | 7/1998 | Pavlin et al. | |
| 5,788,626 | A | 8/1998 | Thompson | |
| 5,788,979 | A | 8/1998 | Alt et al. | |
| 5,800,392 | A | 9/1998 | Racchini | |
| 5,820,917 | A | 10/1998 | Tuch | |
| 5,823,996 | A | 10/1998 | Sparks | |
| 5,824,048 | A | 10/1998 | Tuch | |
| 5,824,049 | A | 10/1998 | Ragheb et al. | |
| 5,830,178 | A | 11/1998 | Jones et al. | |
| 5,833,659 | A | 11/1998 | Kranys | |
| 5,836,965 | A | 11/1998 | Jendersee et al. | |
| 5,837,008 | A | 11/1998 | Berg et al. | |
| 5,837,313 | A | 11/1998 | Ding et al. | |
| 5,843,172 | A | 12/1998 | Yan | |
| 5,849,859 | A | 12/1998 | Acemoglu | |
| 5,851,508 | A | 12/1998 | Greff et al. | |
| 5,854,376 | A | 12/1998 | Higashi | |

| | | | | |
|---|---|---|---|---|
| 5,855,598 | A | | 1/1999 | Pinchuk |
| 5,855,600 | A | | 1/1999 | Alt |
| 5,855,684 | A | | 1/1999 | Bergmann |
| 5,858,746 | A | | 1/1999 | Hubbell et al. |
| 5,865,814 | A | | 2/1999 | Tuch |
| 5,869,127 | A | | 2/1999 | Zhong |
| 5,873,904 | A | | 2/1999 | Ragheb et al. |
| 5,876,433 | A | | 3/1999 | Lunn |
| 5,877,224 | A | | 3/1999 | Brocchini et al. |
| 5,879,713 | A | | 3/1999 | Roth et al. |
| 5,891,108 | A | | 4/1999 | Leone et al. |
| 5,891,507 | A | | 4/1999 | Jayaraman |
| 5,895,407 | A | | 4/1999 | Jayaraman |
| 5,897,911 | A | | 4/1999 | Loeffler |
| 5,902,631 | A | | 5/1999 | Wang et al. |
| 5,902,875 | A | | 5/1999 | Roby et al. |
| 5,905,168 | A | | 5/1999 | Dos Santos et al. |
| 5,910,564 | A | | 6/1999 | Gruning et al. |
| 5,911,752 | A | | 6/1999 | Dustrude et al. |
| 5,914,387 | A | | 6/1999 | Roby et al. |
| 5,919,893 | A | | 7/1999 | Roby et al. |
| 5,922,393 | A | | 7/1999 | Jayaraman |
| 5,925,720 | A | | 7/1999 | Kataoka et al. |
| 5,928,279 | A | | 7/1999 | Shannon et al. |
| 5,932,299 | A | | 8/1999 | Katoot |
| 5,935,135 | A | | 8/1999 | Bramfitt et al. |
| 5,948,018 | A | | 9/1999 | Dereume et al. |
| 5,955,509 | A | | 9/1999 | Webber et al. |
| 5,958,385 | A | | 9/1999 | Tondeur et al. |
| 5,962,138 | A | | 10/1999 | Kolluri et al. |
| 5,968,091 | A | | 10/1999 | Pinchuk et al. |
| 5,971,954 | A | | 10/1999 | Conway et al. |
| 5,972,027 | A | | 10/1999 | Johnson |
| 5,980,928 | A | | 11/1999 | Terry |
| 5,980,972 | A | * | 11/1999 | Ding ......................... 427/2.24 |
| 5,984,449 | A | | 11/1999 | Tajika et al. |
| 5,997,517 | A | | 12/1999 | Whitbourne |
| 6,010,530 | A | | 1/2000 | Goicoechea |
| 6,010,573 | A | | 1/2000 | Bowlin |
| 6,011,125 | A | | 1/2000 | Lohmeijer et al. |
| 6,013,099 | A | | 1/2000 | Dinh et al. |
| 6,015,541 | A | | 1/2000 | Greff et al. |
| 6,030,371 | A | | 2/2000 | Pursley |
| 6,033,582 | A | | 3/2000 | Lee et al. |
| 6,034,204 | A | | 3/2000 | Mohr et al. |
| 6,042,875 | A | | 3/2000 | Ding et al. |
| 6,045,899 | A | | 4/2000 | Wang et al. |
| 6,051,576 | A | | 4/2000 | Ashton et al. |
| 6,051,648 | A | | 4/2000 | Rhee et al. |
| 6,054,553 | A | | 4/2000 | Groth et al. |
| 6,056,993 | A | | 5/2000 | Leidner et al. |
| 6,059,714 | A | | 5/2000 | Armini et al. |
| 6,060,451 | A | | 5/2000 | DiMaio et al. |
| 6,060,518 | A | | 5/2000 | Kabanov et al. |
| 6,068,202 | A | | 5/2000 | Hynes et al. |
| 6,071,305 | A | | 6/2000 | Brown et al. |
| 6,080,488 | A | | 6/2000 | Hostettler et al. |
| 6,096,070 | A | | 8/2000 | Ragheb et al. |
| 6,099,562 | A | | 8/2000 | Ding et al. |
| 6,106,889 | A | | 8/2000 | Jayaraman |
| 6,110,188 | A | | 8/2000 | Narciso, Jr. |
| 6,110,483 | A | | 8/2000 | Whitbourne et al. |
| 6,113,629 | A | | 9/2000 | Ken |
| 6,120,491 | A | | 9/2000 | Kohn et al. |
| 6,120,536 | A | | 9/2000 | Ding et al. |
| 6,120,788 | A | | 9/2000 | Barrows |
| 6,120,847 | A | | 9/2000 | Yang et al. |
| 6,120,904 | A | | 9/2000 | Hostettler et al. |
| 6,121,027 | A | | 9/2000 | Clapper et al. |
| 6,126,686 | A | | 10/2000 | Badylak et al. |
| 6,129,755 | A | | 10/2000 | Mathis et al. |
| 6,129,761 | A | | 10/2000 | Hubbell |
| 6,136,333 | A | | 10/2000 | Cohn et al. |
| 6,140,127 | A | | 10/2000 | Sprague |
| 6,140,431 | A | | 10/2000 | Kinker et al. |
| 6,143,354 | A | | 11/2000 | Koulik et al. |
| 6,143,370 | A | | 11/2000 | Panagiotou et al. |
| 6,153,252 | A | | 11/2000 | Hossainy et al. |
| 6,156,373 | A | | 12/2000 | Zhong et al. |
| 6,159,978 | A | | 12/2000 | Myers et al. |
| 6,165,212 | A | | 12/2000 | Dereume et al. |
| 6,165,267 | A | | 12/2000 | Torczynski |
| 6,171,334 | B1 | | 1/2001 | Cox |
| 6,172,167 | B1 | | 1/2001 | Stapert et al. |
| 6,174,329 | B1 | | 1/2001 | Callol et al. |
| 6,177,523 | B1 | | 1/2001 | Reich et al. |
| 6,180,632 | B1 | | 1/2001 | Myers et al. |
| 6,194,034 | B1 | | 2/2001 | Nishi et al. |
| 6,197,013 | B1 | | 3/2001 | Reed et al. |
| 6,203,551 | B1 | | 3/2001 | Wu |
| 6,203,569 | B1 | | 3/2001 | Wijay |
| 6,206,915 | B1 | | 3/2001 | Fagan et al. |
| 6,211,249 | B1 | | 4/2001 | Cohn et al. |
| 6,214,115 | B1 | | 4/2001 | Taylor et al. |
| 6,214,901 | B1 | | 4/2001 | Chudzik et al. |
| 6,228,072 | B1 | | 5/2001 | Omaleki et al. |
| 6,231,600 | B1 | | 5/2001 | Zhong |
| 6,235,340 | B1 | | 5/2001 | Lee et al. |
| 6,240,616 | B1 | | 6/2001 | Yan |
| 6,244,575 | B1 | | 6/2001 | Vaartstra et al. |
| 6,245,099 | B1 | | 6/2001 | Edwin et al. |
| 6,245,753 | B1 | | 6/2001 | Byun et al. |
| 6,245,760 | B1 | | 6/2001 | He et al. |
| 6,248,129 | B1 | | 6/2001 | Froix |
| 6,248,398 | B1 | | 6/2001 | Talieh et al. |
| 6,251,136 | B1 | | 6/2001 | Guruwaiya et al. |
| 6,254,632 | B1 | | 7/2001 | Wu et al. |
| 6,258,121 | B1 | | 7/2001 | Yang et al. |
| 6,258,371 | B1 | | 7/2001 | Koulik et al. |
| 6,261,320 | B1 | | 7/2001 | Tam et al. |
| 6,262,034 | B1 | | 7/2001 | Mathiowitz et al. |
| 6,270,504 | B1 | | 8/2001 | Lorentzen Cornelius et al. |
| 6,270,788 | B1 | | 8/2001 | Koulik et al. |
| 6,273,878 | B1 | | 8/2001 | Muni |
| 6,273,908 | B1 | | 8/2001 | Ndondo-Lay |
| 6,273,910 | B1 | | 8/2001 | Limon |
| 6,273,913 | B1 | | 8/2001 | Wright et al. |
| 6,277,449 | B1 | | 8/2001 | Kolluri et al. |
| 6,279,368 | B1 | | 8/2001 | Escano et al. |
| 6,283,947 | B1 | | 9/2001 | Mirzaee |
| 6,283,949 | B1 | | 9/2001 | Roorda |
| 6,284,305 | B1 | | 9/2001 | Ding et al. |
| 6,287,249 | B1 | | 9/2001 | Tam et al. |
| 6,287,628 | B1 | | 9/2001 | Hossainy et al. |
| 6,299,604 | B1 | | 10/2001 | Ragheb et al. |
| 6,306,165 | B1 | | 10/2001 | Patnaik et al. |
| 6,306,176 | B1 | | 10/2001 | Whitbourne |
| 6,322,847 | B1 | | 11/2001 | Zhong et al. |
| 6,331,191 | B1 | | 12/2001 | Chobotov |
| 6,331,313 | B1 | | 12/2001 | Wong et al. |
| 4,733,665 | C2 | | 1/2002 | Palmaz |
| 6,335,029 | B1 | | 1/2002 | Kamath et al. |
| 6,344,035 | B1 | | 2/2002 | Chudzik et al. |
| 6,346,110 | B2 | | 2/2002 | Wu |
| 6,358,556 | B1 | | 3/2002 | Ding et al. |
| 6,358,567 | B2 | | 3/2002 | Pham et al. |
| 6,364,903 | B2 | | 4/2002 | Tseng et al. |
| 6,368,658 | B1 | | 4/2002 | Schwarz et al. |
| 6,372,283 | B1 | | 4/2002 | Shim et al. |
| 6,379,381 | B1 | | 4/2002 | Hossainy et al. |
| 6,383,215 | B1 | | 5/2002 | Sass |
| 6,387,118 | B1 | | 5/2002 | Hanson |
| 6,387,379 | B1 | | 5/2002 | Goldberg et al. |
| 6,395,326 | B1 | | 5/2002 | Castro et al. |
| 6,407,009 | B1 | | 6/2002 | You et al. |
| 6,416,543 | B1 | | 7/2002 | Hilaire et al. |

| | | | |
|---|---|---|---|
| 6,419,692 | B1 | 7/2002 | Yang et al. |
| 6,435,798 | B1 | 8/2002 | Satoh |
| 6,440,221 | B2 | 8/2002 | Shamouilian et al. |
| 6,451,373 | B1 | 9/2002 | Hossainy et al. |
| 6,468,298 | B1 | 10/2002 | Pelton |
| 6,475,779 | B2 | 11/2002 | Mathiowitz et al. |
| 6,482,834 | B2 | 11/2002 | Spada et al. |
| 6,494,862 | B1 | 12/2002 | Ray et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,506,437 | B1 | 1/2003 | Harish et al. |
| 6,517,534 | B1 | 2/2003 | McGovern et al. |
| 6,517,889 | B1 | 2/2003 | Jayaraman |
| 6,521,284 | B1 | 2/2003 | Parsons et al. |
| 6,524,347 | B1 | 2/2003 | Myers et al. |
| 6,527,801 | B1 | 3/2003 | Dutta |
| 6,527,863 | B1 | 3/2003 | Pacetti et al. |
| 6,528,526 | B1 | 3/2003 | Myers et al. |
| 6,530,950 | B1 | 3/2003 | Alvarado et al. |
| 6,530,951 | B1 | 3/2003 | Bates et al. |
| 6,534,112 | B1 | 3/2003 | Bouchier et al. |
| 6,540,776 | B2 | 4/2003 | Sanders Millare et al. |
| 6,544,223 | B1 | 4/2003 | Kokish |
| 6,544,543 | B1 | 4/2003 | Mandrusov et al. |
| 6,544,582 | B1 | 4/2003 | Yoe |
| 6,555,157 | B1 | 4/2003 | Hossainy |
| 6,558,733 | B1 | 5/2003 | Hossainy et al. |
| 6,562,136 | B1 | 5/2003 | Chappa et al. |
| 6,565,659 | B1 | 5/2003 | Pacetti et al. |
| 6,572,644 | B1 | 6/2003 | Moein |
| 6,572,651 | B1 | 6/2003 | De Scheerder et al. |
| 6,575,933 | B1 | 6/2003 | Wittenberger et al. |
| 6,585,755 | B2 | 7/2003 | Jackson et al. |
| 6,585,765 | B1 | 7/2003 | Hossainy et al. |
| 6,585,926 | B1 | 7/2003 | Mirzaee |
| 6,605,154 | B1 | 8/2003 | Villareal |
| 6,610,087 | B1 | 8/2003 | Zarbatany et al. |
| 6,613,432 | B2 | 9/2003 | Zamora et al. |
| 6,616,765 | B1 | 9/2003 | Castro et al. |
| 6,620,617 | B2 | 9/2003 | Mathiowitz et al. |
| 6,623,448 | B2 | 9/2003 | Slater |
| 6,625,486 | B2 | 9/2003 | Lundkvist et al. |
| 6,641,611 | B2 | 11/2003 | Jayaraman |
| 6,645,135 | B1 | 11/2003 | Bhat |
| 6,645,195 | B1 | 11/2003 | Bhat et al. |
| 6,656,216 | B1 | 12/2003 | Hossainy et al. |
| 6,656,506 | B1 | 12/2003 | Wu et al. |
| 6,660,034 | B1 | 12/2003 | Mandrusov et al. |
| 6,663,662 | B2 | 12/2003 | Pacetti et al. |
| 6,663,880 | B1 | 12/2003 | Roorda et al. |
| 6,666,880 | B1 | 12/2003 | Chiu et al. |
| 6,673,154 | B1 | 1/2004 | Pacetti et al. |
| 6,673,385 | B1 | 1/2004 | Ding et al. |
| 6,676,700 | B1 | 1/2004 | Jacobs et al. |
| 6,682,771 | B2 | 1/2004 | Zhong et al. |
| 6,689,099 | B2 | 2/2004 | Mirzaee |
| 6,689,350 | B2 | 2/2004 | Uhrich |
| 6,695,920 | B1 | 2/2004 | Pacetti et al. |
| 6,706,013 | B1 | 3/2004 | Bhat et al. |
| 6,709,514 | B1 | 3/2004 | Hossainy |
| 6,712,845 | B2 | 3/2004 | Hossainy |
| 6,713,119 | B2 | 3/2004 | Hossainy et al. |
| 6,716,444 | B1 | 4/2004 | Castro et al. |
| 6,723,120 | B2 | 4/2004 | Yan |
| 6,723,373 | B1 | 4/2004 | Narayanan et al. |
| 6,730,064 | B2 | 5/2004 | Ragheb et al. |
| 6,733,768 | B2 | 5/2004 | Hossainy et al. |
| 6,740,040 | B1 | 5/2004 | Mandrusov et al. |
| 6,743,462 | B1 | 6/2004 | Pacetti |
| 6,746,773 | B2 | 6/2004 | Llanos et al. |
| 6,749,626 | B1 | 6/2004 | Bhat et al. |
| 6,753,071 | B1 | 6/2004 | Pacetti et al. |
| 6,758,859 | B1 | 7/2004 | Dang et al. |
| 6,759,054 | B2 | 7/2004 | Chen et al. |
| 6,764,505 | B1 | 7/2004 | Hossainy et al. |
| 6,776,796 | B2 | 8/2004 | Falotico et al. |
| 6,780,424 | B2 | 8/2004 | Claude |
| 6,790,228 | B2 | 9/2004 | Hossainy et al. |
| 6,818,063 | B1 | 11/2004 | Kerrigan |
| 6,824,559 | B2 | 11/2004 | Michal |
| 6,860,946 | B2 | 3/2005 | Hossainy et al. |
| 6,887,510 | B2 | 5/2005 | Villareal |
| 6,890,583 | B2 | 5/2005 | Chudzik et al. |
| 6,955,723 | B2 | 10/2005 | Pacetti et al. |
| 2001/0007083 | A1 | 7/2001 | Roorda |
| 2001/0029351 | A1 | 10/2001 | Falotico et al. |
| 2001/0037145 | A1 | 11/2001 | Guruwaiya et al. |
| 2002/0005206 | A1 | 1/2002 | Falotico et al. |
| 2002/0007213 | A1 | 1/2002 | Falotico et al. |
| 2002/0007214 | A1 | 1/2002 | Falotico |
| 2002/0007215 | A1 | 1/2002 | Falotico et al. |
| 2002/0050220 | A1 | 5/2002 | Schueller et al. |
| 2002/0051730 | A1 | 5/2002 | Bodnar et al. |
| 2002/0077693 | A1 | 6/2002 | Barclay et al. |
| 2002/0082679 | A1 | 6/2002 | Sirhan et al. |
| 2002/0087123 | A1 | 7/2002 | Hossainy et al. |
| 2002/0091433 | A1 | 7/2002 | Ding et al. |
| 2002/0111590 | A1 | 8/2002 | Davila et al. |
| 2002/0165608 | A1 | 11/2002 | Llanos et al. |
| 2002/0176849 | A1 | 11/2002 | Slepian |
| 2002/0183581 | A1 | 12/2002 | Yoe et al. |
| 2002/0188037 | A1 | 12/2002 | Chudzik et al. |
| 2002/0188277 | A1 | 12/2002 | Roorda et al. |
| 2003/0004141 | A1 | 1/2003 | Brown |
| 2003/0028243 | A1 | 2/2003 | Bates et al. |
| 2003/0028244 | A1 | 2/2003 | Bates et al. |
| 2003/0031780 | A1 | 2/2003 | Chudzik et al. |
| 2003/0032767 | A1 | 2/2003 | Tada et al. |
| 2003/0036794 | A1 | 2/2003 | Ragheb et al. |
| 2003/0039689 | A1 | 2/2003 | Chen et al. |
| 2003/0040712 | A1 | 2/2003 | Ray et al. |
| 2003/0040790 | A1 | 2/2003 | Furst |
| 2003/0059520 | A1 | 3/2003 | Chen et al. |
| 2003/0060877 | A1 | 3/2003 | Falotico et al. |
| 2003/0065377 | A1 | 4/2003 | Davila et al. |
| 2003/0072868 | A1 | 4/2003 | Harish et al. |
| 2003/0073961 | A1 | 4/2003 | Happ |
| 2003/0083646 | A1 | 5/2003 | Sirhan et al. |
| 2003/0083739 | A1 | 5/2003 | Cafferata |
| 2003/0088307 | A1 | 5/2003 | Shulze et al. |
| 2003/0097088 | A1 | 5/2003 | Pacetti |
| 2003/0097173 | A1 | 5/2003 | Dutta |
| 2003/0105518 | A1 | 6/2003 | Dutta |
| 2003/0113439 | A1 | 6/2003 | Pacetti et al. |
| 2003/0150380 | A1 | 8/2003 | Yoe |
| 2003/0158517 | A1 | 8/2003 | Kokish |
| 2003/0190406 | A1 | 10/2003 | Hossainy et al. |
| 2003/0211230 | A1 | 11/2003 | Pacetti et al. |
| 2003/0215564 | A1 | 11/2003 | Heller et al. |
| 2004/0018296 | A1 | 1/2004 | Castro et al. |
| 2004/0029952 | A1 | 2/2004 | Chen et al. |
| 2004/0047978 | A1 | 3/2004 | Hossainy et al. |
| 2004/0047980 | A1 | 3/2004 | Pacetti et al. |
| 2004/0052858 | A1 | 3/2004 | Wu et al. |
| 2004/0052859 | A1 | 3/2004 | Wu et al. |
| 2004/0054104 | A1 | 3/2004 | Pacetti |
| 2004/0060508 | A1 | 4/2004 | Pacetti et al. |
| 2004/0062853 | A1 | 4/2004 | Pacetti et al. |
| 2004/0063805 | A1 | 4/2004 | Pacetti et al. |
| 2004/0071861 | A1 | 4/2004 | Mandrusov et al. |
| 2004/0072922 | A1 | 4/2004 | Hossainy et al. |
| 2004/0073298 | A1 | 4/2004 | Hossainy |
| 2004/0086542 | A1 | 5/2004 | Hossainy et al. |
| 2004/0086550 | A1 | 5/2004 | Roorda et al. |
| 2004/0096504 | A1 | 5/2004 | Michal |

| | | | |
|---|---|---|---|
| 2004/0098117 A1 | 5/2004 | Hossainy et al. |
| 2004/0191405 A1 | 9/2004 | Kerrigan |
| 2004/0213893 A1 | 10/2004 | Boulais |
| 2005/0069630 A1 | 3/2005 | Fox et al. |
| 2005/0074544 A1 | 4/2005 | Pacetti et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 627 226 | 12/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 875 218 | 11/1998 |
| EP | 0 879 595 | 11/1998 |
| EP | 0 897 701 | 2/1999 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 05009726 A | 1/1993 |
| JP | 11299901 | 11/1999 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 90/01969 | 3/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/16386 | 4/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/00112 | 1/2001 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

U.S. Appl. No. 09/997,390, filed Nov. 30, 2001, Pacetti.
U.S. Appl. No. 10/040,538, filed Dec. 28, 2001, Pacetti et al.
U.S. Appl. No. 10/255,913, filed Sep. 26, 2002, Tang et al.
U.S. Appl. No. 10/262,161, filed Sep. 30, 2002, Pacetti.
U.S. Appl. No. 10/266,479, filed Oct. 8, 2002, Hossainy.
U.S. Appl. No. 10/304,669, filed Nov. 25, 2002, Madriaga et al.
U.S. Appl. No. 10/319,042, filed Dec. 12, 2002, Van Sciver et al.
U.S. Appl. No. 10/330,412, filed Dec. 27, 2002, Hossainy et al.
U.S. Appl. No. 10/376,027, filed Feb. 26, 2003, Kokish et al.
U.S. Appl. No. 10/438,378, filed May 15, 2003, Esbeck et al.
U.S. Appl. No. 10/660,853, filed Sep. 12, 2003, Pacetti et al.
U.S. Appl. No. 10/729,551, filed Dec. 5, 2003, Pacetti.
U.S. Appl. No. 10/729,728, filed Dec. 5, 2003, Pacetti.
U.S. Appl. No. 10/750,312, filed Dec. 30, 2003, Desnoyer et al.
U.S. Appl. No. 10/805,047, filed Mar. 18, 2004, Yip et al.
U.S. Appl. No. 10/813,845, filed Mar. 30, 2004, Pacetti.
U.S. Appl. No. 10/817,642, filed Apr. 2, 2004, Kerrigan.
U.S. Appl. No. 11/193,849, filed Jul. 28, 2005, Harold et al.
U.S. Appl. No. 11/222,052, filed Sep. 7, 2005, Pacetti et al.
U.S. Appl. No. 11/222,053, filed Sep. 7, 2005, Pacetti et al.
U.S. Appl. No. 11/233,991, filed Sep. 22, 2005, Hossainy.
Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003, (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Coating Techniques, *Air Knife Coating*, http://www.ferron-magnetic.co.uk/coatings/airknife.htm, 1 page, printed Jul. 1, 2003.
Coating Techniques, *Gap Coating*, http://www.ferron-magnetic.co.uk/coatinqs/knife.htm, 1 page, printed Jul. 1, 2003.
Coating Techniques, *Gravure Coating*, http://www.ferron-magnetic.co.uk/coatings/gravure.htm, 2 pages, printed Jul. 1, 2003.
Coating Techniques, *Reverse Roll Coating*, http://www.ferron-magnetic.co.uk/coatings/revroll.htm, 2 pages, printed Jul. 1, 2003.

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Forrester et al., *A Paradigm for Restenosis Based on Cell Biology: Clues for the Development of New Preventive Therapies*; J. Am. Coll. Cardio. 1991; 17:758-769.

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Illbruck Sealant Systems, *Application: Window and Perimeter Silicone*, http://www.willseal.com/usa/produktuebersicht/dichtstoffe/perwindow/verlege_anleitung . . . , printed Nov. 29, 2004 (3 pages).

Inoue et al., *An AB block copolymer of oligo(methyl methacrylate) and poly(acrylic acid) for micellar delivery of hydrophobic drugs*, Journal of Controlled Release 51:221-229 (1998).

International Search Report and Written Opinion, dated Mar. 1, 2005 for PCT Application No. PCT/US2004/031185, filed Sep. 22, 2004 (14 pages).

Kataoka et al., *Block copolymer micelles as vehicles for drug delivery*, Journal of Controlled Release 24:119-132 (1993).

Kim, *Solid State Sintering*, AMSE 604 Solid State Reactions and Sintering, Electroceramic laboratory in Dept. of Materials Science & Engineering, POSTECH, Pohang University of Science and Technology (20 pages).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*; Chemical Abstract 125:212307 (1996).

van Beusekom et al., *Coronary stent coatings*, Coronary Artery Disease 5(7):590-596 (Jul. 1994).

Van Iseghem, *Important Concepts on Coating Plastics From a Formulator's Perspective*, Modern Paint and Coatings, pp. 30-38 (Feb. 1998).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

CLAMP MANDREL FIXTURE AND A METHOD OF USING THE SAME TO MINIMIZE COATING DEFECTS

CROSS REFERENCE

This is a divisional application of application Ser. No. 10/319,042 filed on Dec. 12, 2002 now U.S. Pat. No. 7,074,276.

BACKGROUND OF THE INVENTION

1. Field of the Invention

This invention relates to a clamp mandrel fixture for supporting a stent during the application of a coating composition.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giantruco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral gaps or openings 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY

A device for supporting a stent during the application of a coating substance to the stent is provided. In one embodiment, the device comprises a base, a mandrel extending from the base for penetrating at least partially through the longitudinal bore of the stent, and clamp elements extending from the base, the clamp elements configured to have an open configuration for allowing the mandrel to be inserted into the longitudinal bore of the stent, and a closed configuration for securing the stent on the mandrel during the application of the coating substance to the stent.

The outer diameter of the mandrel can be smaller than the inner diameter of the stent. In one variation, the base can include an indented portion, wherein each of the clamp elements can include a first segment extending over the indented portion of the base and a second segment extending out from the base such that an application of a force to the first segments of the clamp elements over the indented portion of the base causes the second segments to move away from each other towards the open configuration and the release of the force results in the second segments of the clamp elements to retract back towards each other. In the closed configuration, the clamp elements can compress against the mandrel. In one embodiment, each of the clamp elements includes a first segment having a first length and a second segment having a second length, shorter than the first length, the second segments being bent in an inwardly direction towards the mandrel for engagement with the mandrel when the clamp elements are in the closed configuration. The first segments does not contact the stent when the clamp elements are in the closed configuration. Moreover, the stent should not be capable of contacting the base when the stent is secured by the clamp elements on the mandrel.

In accordance with another embodiment, the device comprises a mandrel capable of extending at least partially through the hollow body of a stent, and an arm element for extending through a gaped region between the struts of the stent for holding the stent on the mandrel during the application of a coating composition to the stent. In one embodiment, the device additionally includes a base member, wherein the mandrel extends from a center region of an end of the base member and the arm element extends from an edge of the end of the base member. The arm element can be characterized by a generally "L" shaped configuration having a long segment and a short segment. The long segment of the arm element can be generally parallel to the mandrel and the short segment of the arm element can be generally perpendicular to the mandrel, the short segment of the arm being configured to extend through the gaped region of the stent to compress against the mandrel. In one variation, the diameter of the mandrel plus the length of the short segment of the arm element is greater than the outer diameter of the stent so as to prevent the stent from making contact with the long segment of the arm element during the application of the coating composition. The long segment of the arm element is capable of flexibly bending for engaging and disengaging the short segment of the arm element from the mandrel. In one embodiment, in a natural position, the long segment of the arm element is in a generally linear configuration allowing the short segment of the arm element to be compressed against the mandrel. In another embodiment, the length of the mandrel as measured from the end of the base member is longer than the length of the long segment of the arm element as measured from the end of the base member.

In accordance with yet another embodiment of the invention, a system for supporting a stent during the application of a coating substance to the stent is provided. The system comprises a base member and a first clamp member and a second clamp member extending from the base member, wherein a segment of each clamp member is configured to penetrate into a gaped region of a scaffolding network of the stent for supporting the stent on the base member during the application of the coating substance. In one embodiment, a motor assembly is connected to the base member for rotating the stent about the longitudinal axis of the stent during the application of the coating substance. In another embodiment, a mandrel extends from the base member for being inserted through the hollow tubular body of the stent, wherein the segments of the clamp members that are configured to penetrate into the gaped regions of the scaffolding network are configured to engage with the mandrel for securing the stent on the mandrel. The system can also include a nozzle assembly for spraying the coating substance onto the stent.

In accordance with yet another embodiment, a device for supporting a stent during the application of a coating substance to the stent is provided, the device comprises base member having a indented portion and a clamp member having a first segment disposed on the base member and extending over the indented portion of the base member, and a second segment extending out from one end of the base member for engagement with the stent. The application of pressure on a region of the first segment extending over the indented portion of the base member causes the clamp member to extend in an outwardly direction. The device can additionally include a second clamp member having a first segment disposed on the base member and extending over the indented portion of the base member, and a second segment extending out from the one end of the base member for engagement with the stent, wherein the application of a pressure on the first segments of the first and second clamp members causes the second segments of the first and second clamp members to bias away from one another and the release of the pressure from the first segments causes the first and second clamp members to bias towards each other for engagement of the stent.

A method of coating a stent is also provided comprising positioning the stent on any of the embodiment of the support device and applying a coating composition to the stent.

DETAILED DESCRIPTION

Embodiments of the Mounting Assembly

Figure 1:
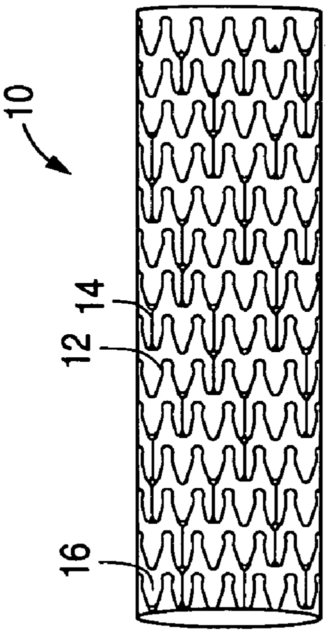
Figure 1 (PRIOR ART)
FIG. 1 illustrates a conventional stent.
Figure 2A:
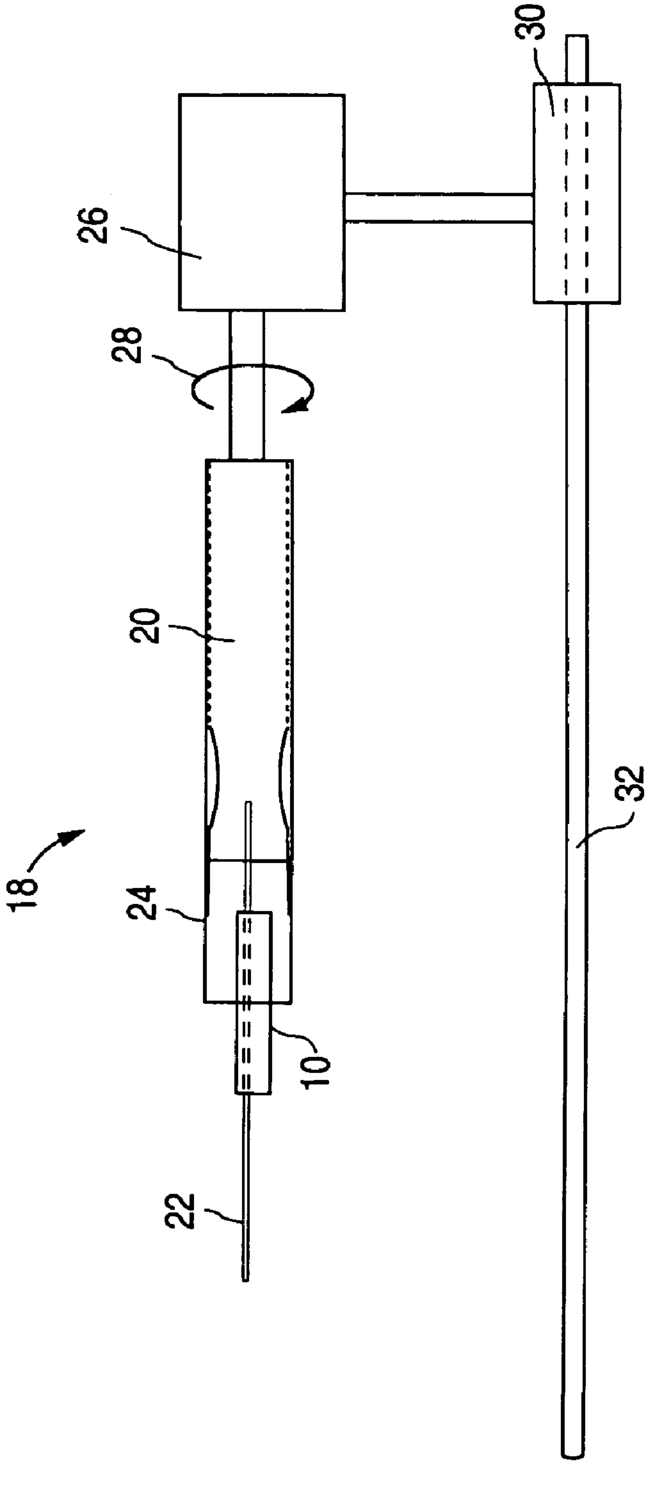
FIG. 2A illustrates a mounting assembly for supporting a stent in accordance with one embodiment of the invention.

Referring to FIG. 2A, a mounting assembly 18 for supporting stent 10 is illustrated to include a base 20, a center pin or mandrel 22, and clamp or arm elements 24. Base 20 can connect to a motor 26, which provides rotational motion to mounting assembly 18, as depicted by arrow 28, during the coating process. Another motor 30 can also be provided for moving mounting assembly 18 and thus stent 10 in a linear direction, back and forth, along a rail 32.

Figure 2B:
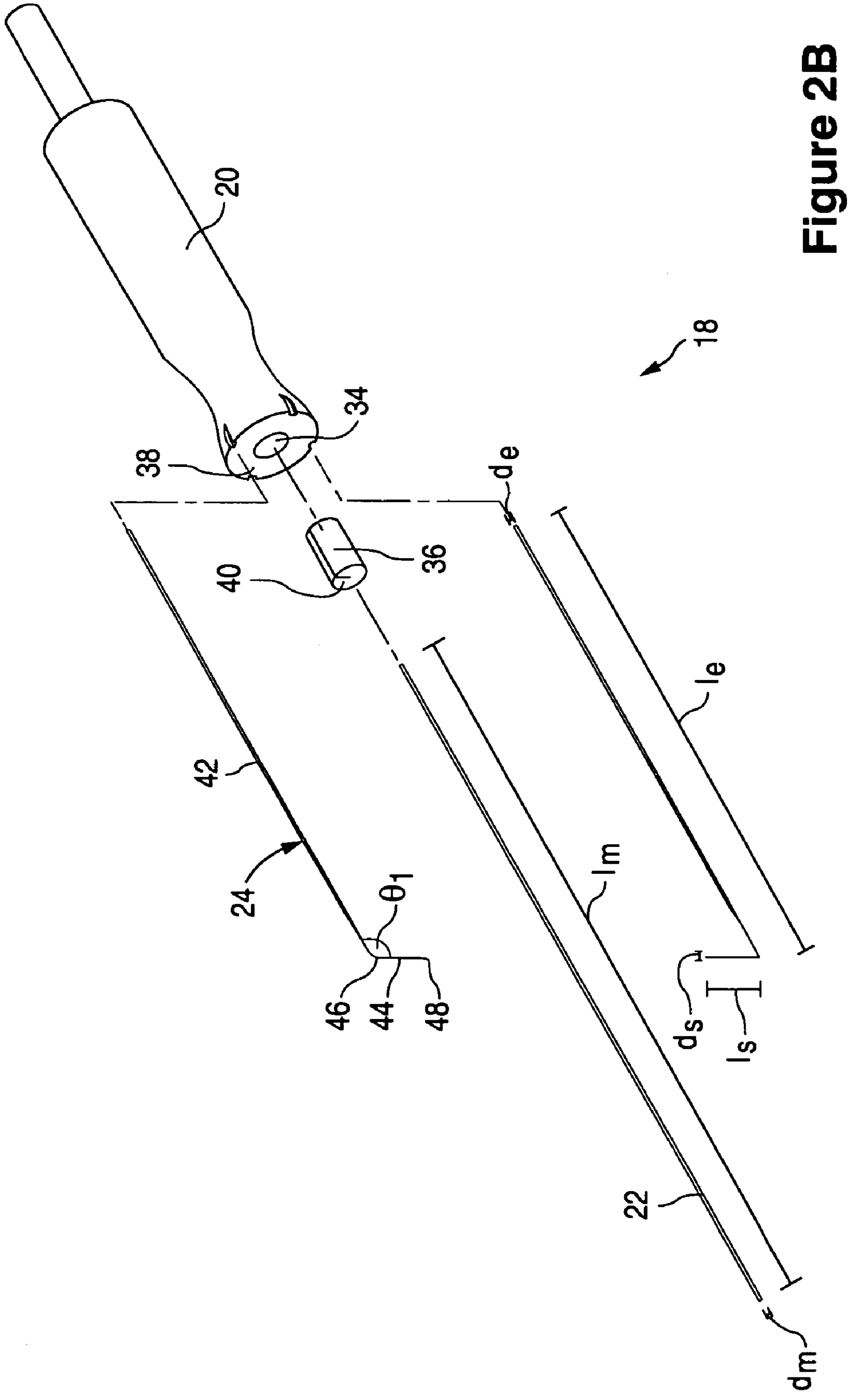
FIG. 2B illustrates an expanded perspective view of the mounting assembly in accordance with one embodiment of the present invention.

Mandrel 22 extends longitudinally from base 20, for example from a central region of the end of base 20. In accordance with one embodiment, mandrel 22 and base 20 can be manufactured as a single component. Alternatively, mandrel 22 and base 20 can be manufactured separately and later coupled to one another. In such an embodiment, base 20 can include a bore 34 for receiving mandrel 22, as illustrated in FIG. 2B. Mandrel 22 can be press fitted into bore 34 or otherwise coupled to base 20 via, for example, welding or adhesives. In the depicted embodiment, mounting assembly 18 additionally includes a mandrel holder 36 for receiving mandrel 22. In such an embodiment, mandrel holder 36 can be permanently or temporarily affixed within bore 34 such that surfaces 38 and 40 are flush upon assembly, and mandrel 22 can be, for example, press fit into mandrel holder 36. A mandrel 22 manufactured separately from base 20 can also be disposable.

Mandrel 22 can be of any suitable diameter $d_m$ and any suitable length $l_m$ that will allow for sufficient support of stent 10 during the coating process. Diameter $d_m$ should be small enough to allow maximum room for motion of stent 10, thereby minimizing the possibility that the inner surface of stent 10 will stick to the outer surface of mandrel 22 during the coating process. Diameter $d_m$ should be large enough to provide sufficient support to stent 10 during rotation as well as against any downward forces exerted during the spraying and drying cycles of the coating process. Length $l_m$ should be longer than the length of stent 10 such that mandrel 22 extends beyond the mounted stent 10 at each of its opposing ends. By way of example and not limitation, mandrel 22 can have diameter $d_m$ that is about 20% of the inner diameter of stent 10 and length $l_m$ that is about ⅛ inch longer than the length of stent 10.

Mandrel 22 can be of any material that is capable of supporting stent 10 and that is compatible with the particular coating composition to be applied to stent 10. For example, mandrel 22 can be made of stainless steel, graphite or a composite. In another embodiment, mandrel 22 can be made of nitinol, the super-elastic properties of which allow mandrels 22 of very small diameters $d_m$ to maintain suitable strength and flexibility throughout the coating process.

Mounting assembly 18 is illustrated as having two arms or clamp elements 24 spaced 180° apart and extending from the and edge of the end of the base 20. In commercially useful embodiments, any number of arms 24 in any configuration can be used to adequately support stent 10, and the embodiments of the present invention should not be limited to a mounting assembly 18 having two arms 24 spaced 180° apart as illustrated in the Figures. It should be noted, however, that the more arms 24 employed to support stent 10, the more contact points that exist between mounting assembly 18 and stent 10. In addition, although each arm 24 is depicted in the Figures as a separate component, multiple arms 24 can be formed from a single component. For example, a wire can be bent into a U-shape such that one half of the wire functions as a first arm 24 and the other half of the wire functions as a second arm 24.

Each arm 24 includes an extension portion 42 extending into a support portion 44 at an angle $\phi_1$ via an elbow 46. Angle $\phi_1$ can be at 90 degrees, for example. Extension portion 42 can couple arm 24 to base 20. Arm 24 can be permanently or temporarily affixed to base 20. Support portion 44 extends through opening 16 between struts 12 of mounted stent 10 to facilitate transient contact between mounting assembly 18 and stent 10 during the coating process.

Extension and support portions 42 and 44 of arms 24 can be of any suitable dimensions. Extension portion 42 should have a length $l_e$ suitable to allow positioning of support portion 44 within a preselected opening 16 between struts 12 along mounted stent 10. Although extension portions 42 are illustrated as having the same length $l_e$, extension portions 42 on the same mounting assembly 18 can have different lengths $l_e$ such that their respective support portions 44 are staggered along the length of mounted stent 10. Length $l_s$ of support portions 44 should be such that support tips 48 touch or compress against mandrel 22 when stent 10 is mounted thereon. Support portions 44 that are too short may cause mounted stent 10 to slip off mounting assembly 18 during the coating process, while support portions 44 that are too long run may hinder movement of stent 10 during the coating process. A diameter $d_e$ of extension portion 42 and a diameter $d_s$ of support portion 44 should be capable of providing sufficient support to stent 10 during rotation as well as against any downward forces exerted during the spraying and drying cycles of the coating process while allowing sufficient movement of stent 10 to prevent permanent contact points between arms 24 and stent 10. In one embodiment, diameter $d_e$ of extension portion 42 tapers into a smaller diameter $d_s$ of support portion 44, thereby optimizing both support and movement of mounted stent 10.

As with mandrel 22 discussed above, arms 24 can be of any material that is capable of supporting stent 10 and that is compatible with the particular coating composition to be applied to stent 10. The material of which arms 24 are formed should also be sufficiently flexible to allow bending into a suitable shape as well as to facilitate easy loading and unloading of stent 10.

Arms 24 must be capable of opening and closing about mandrel 22 to facilitate loading and unloading of stent 10. Arms 24 can be opened and closed in any suitable manner. For example, in one embodiment, arms 24 can be manually pulled open and pushed closed by an operator. In another embodiment, arms 24 can be opened by, for example, sliding a ring along arm 24 toward base 20 and can be closed by sliding the ring along arm 24 toward support portion 44.

Figure 3A:
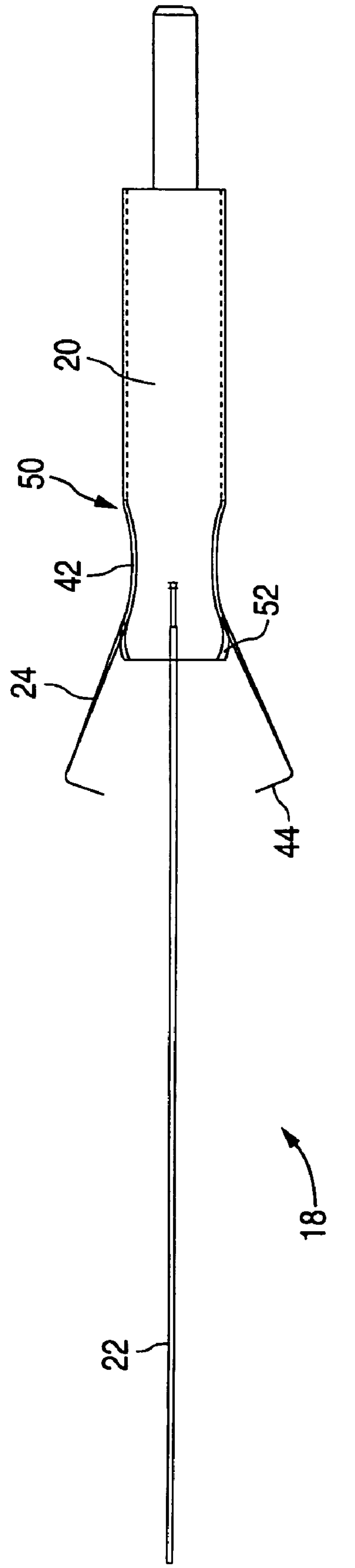
FIG. 3A illustrates the clamp elements or arms of the mounting assembly in an open position in accordance with one embodiment of the present invention.
Figure 3B:
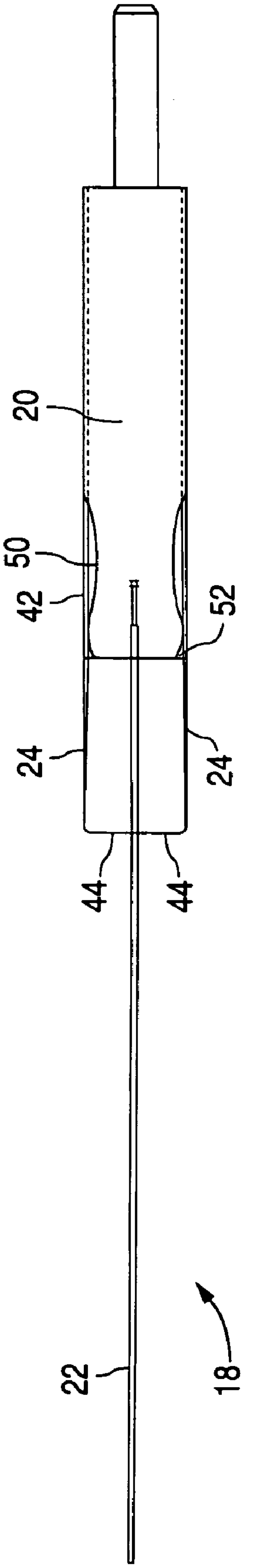
FIG. 3B illustrates the clamp elements or arms of the mounting assembly in a closed position in accordance with one embodiment of the present invention.

FIGS. 3A and 3B illustrate an embodiment in which arms 24 function together as a clamp to facilitate opening and closing. In such an embodiment, base 20 includes an indented portion 50 over which arms 24 extend. Pinching in extension portions 42 over indented portion 50 can open arms 24. Lip 52 further allows extension portions 42 to flexibly spread apart. When pressure is released, extension portions 42 collapse back into a pinched configuration. In this embodiment, the natural position of extension portions 42 should be generally linear and parallel to that of mandrel 22 to allow the biasing of support portion 44 on mandrel 22. The hourglass design of base 20 depicted in the Figures allows an operator to control the opening and closing of clamp-like arms 24 with one hand.

Although mounting assembly 18 is illustrated such that arms 24 are attached to base 20, arms 24 can also be attached to mandrel 22 such that base 20 is not required. In other commercially useful embodiments, mandrel 22 can be supported at its free end during the coating process in any suitable manner. Such support may help mounted stent 10 rotate more concentrically and may also help prevent a slight bend at the free end of mandrel 22 that may otherwise occur due to any downward forces exerted during the spraying and drying cycles of the coating process. In one such embodiment, the free end of mandrel 22 can be stabilized by allowing the free end to rest in a holder such as, for example, a V-block. In another embodiment, a second rotatable base can be coupled to the free end of mandrel 22. The second base can be coupled to a second set of arms. In such an embodiment, at least one base 20 should be disengagable from mandrel 22 so as to allow loading and unloading of stent 10.

Loading a Stent onto the Mounting Assembly

The following description is being provided by way of illustration and is not intended to limit the embodiments of mounting assembly 18, the method of loading stent 10 onto mounting assembly 18, or the method of using mounting assembly 18 to coat stent 10. Referring again to FIG. 3A, clamp-like arms 24 of mounting assembly 18 can be opened by pinching extension portions 42 of arms 24 at depression 50 in the hourglass-shaped base 20 to cause support portions 44 of arms 24 to spread apart. Stent 10 can then be loaded onto mandrel 22 by, for example, holding mounting assembly 18 at an angle (e.g., 15° from horizontal) and sliding stent 10 over mandrel 22 toward base 20. Clamp-like arms 24 can be closed about stent 10 by releasing the pressure applied to extension portions 42, as depicted in FIG. 3B.

Figure 4:
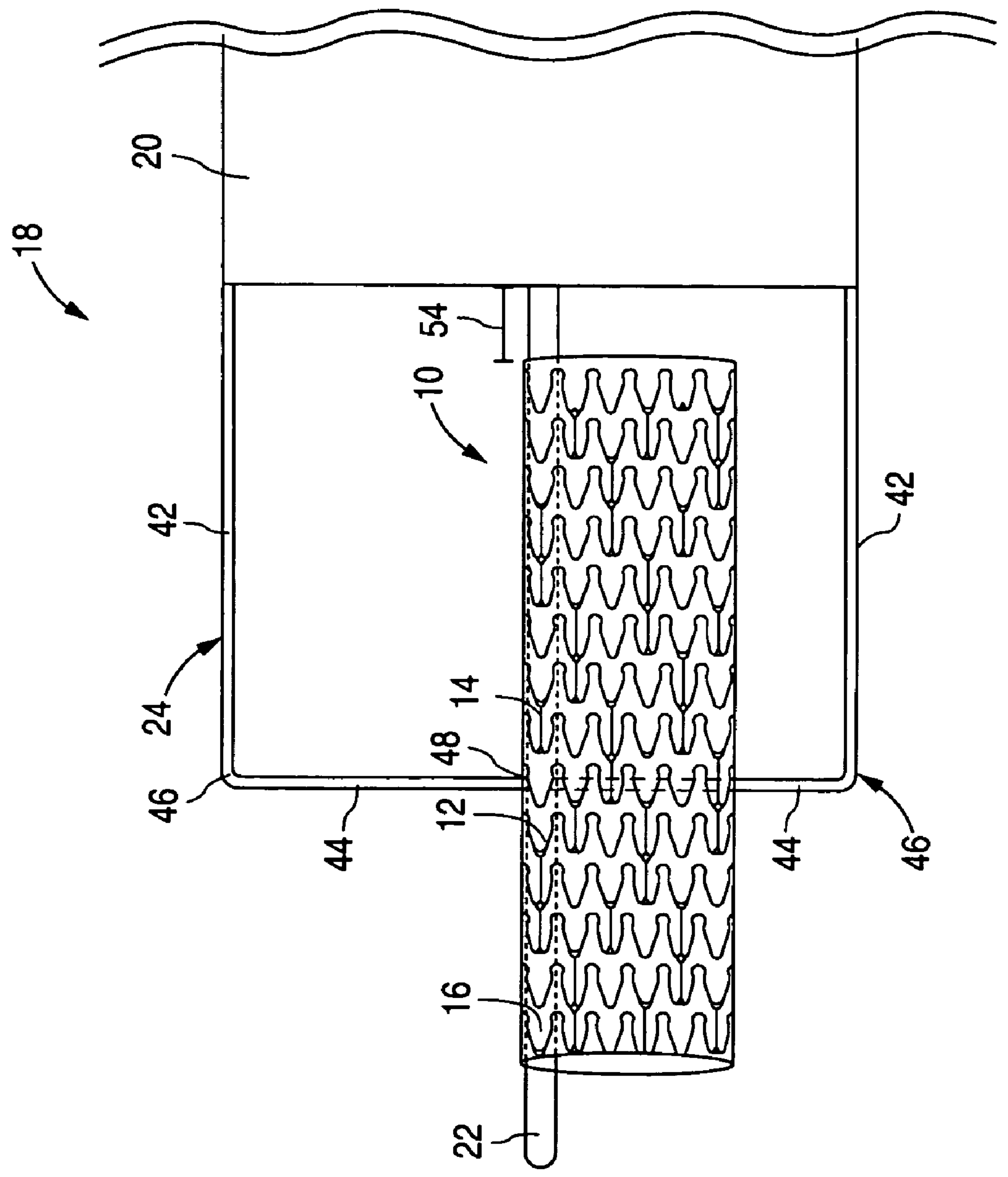
FIG. 4 is a magnified view of the interface between the mounting assembly and the stent in accordance with one embodiment of the present invention.

FIG. 4 depicts the interface between a properly mounted stent 10 and mounting assembly 18. Support portions 44 of arms 24 should protrude through openings 16 between struts 12 of stent 10, and support tips 48 of support portions 44 should touch or compress against mandrel 22. As illustrated, mounted stent 10 should not touch base 20. A gap 54 between base 20 and stent 10 should be maintained to minimize the number of contact points between mounting assembly 18 and stent 10 as well as to maximize the movement of stent 10 during rotation. By way of example and not limitation, gap 54 can be about 1 mm to about 5 mm for stent 10 that is 13 mm to 38 mm long and about 1 mm to about 9 mm for stent 10 that is about 8 mm long. Additionally, as best illustrated by the Figures, diameter $d_m$ of mandrel plus length $l_s$ of support portion 44 should be greater than the outer diameter of stent 10 to prevent stent 10 from contacting extension portions 42.

Figure 5C:
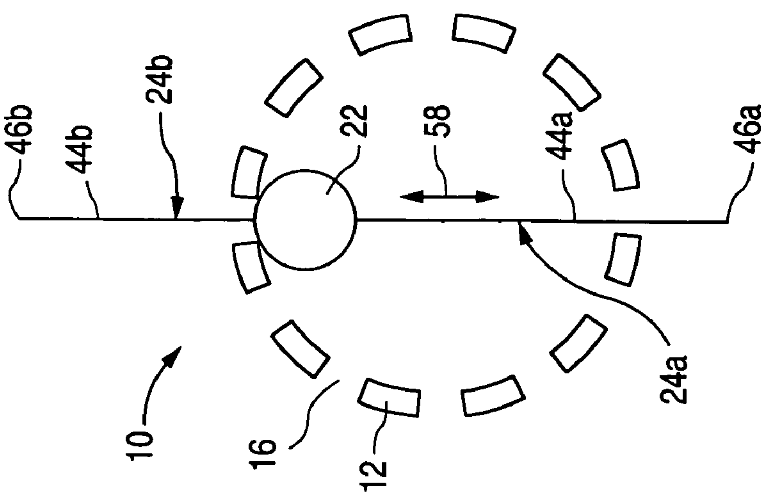
FIGS. 5A-5C are end views illustrating the interface between the mounting assembly and the stent upon rotation during the coating process in accordance with one embodiment of the present invention.
Figure 5B:
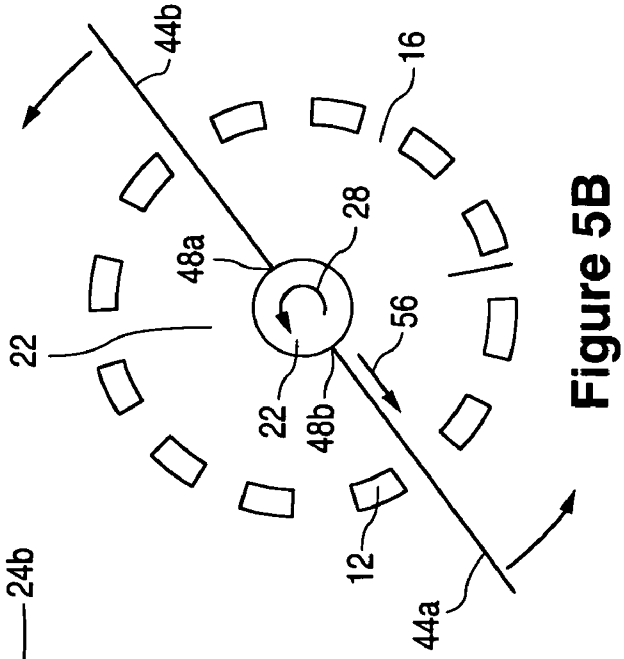
Figure 5A:
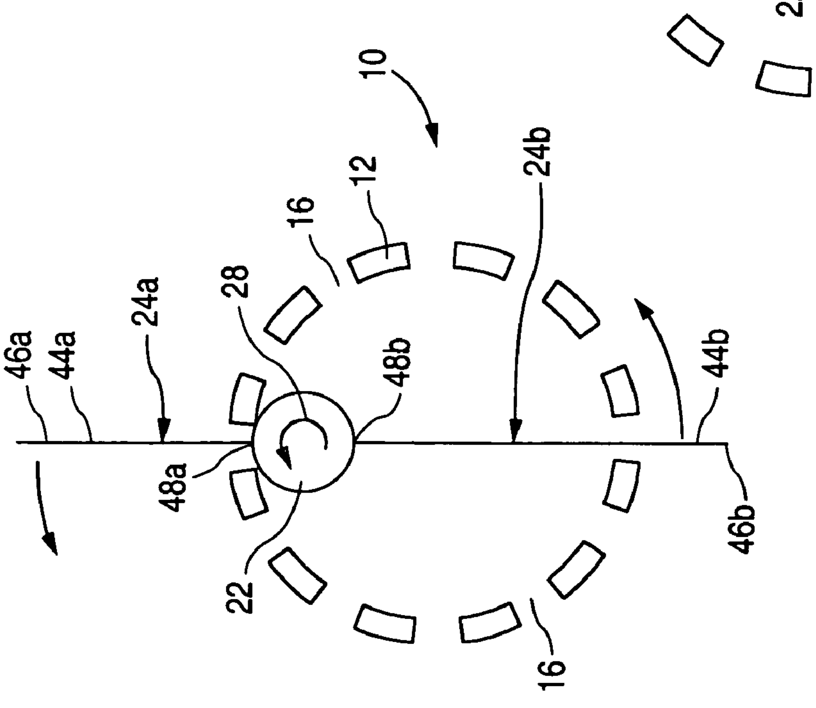

FIGS. 5A-5C illustrate the moving interface between a properly mounted stent 10 and mounting assembly 18 having two arms 24*a* and 24*b* spaced 180° apart upon rotation of mounting assembly 18. As depicted in FIG. 5A, support portions 44*a* and 44*b* of arms 24*a* and 24*b*, respectively, protrude through openings 16 between struts 12 of stent 10, and support tips 48*a* and 48*b* flush against mandrel 22. As mandrel 22 is rotated in the direction of arrow 28, which can be either clock-wise or counter clock-wise, mounted stent 10 also rotates in the direction of arrow 28. As arms 24*a* and 24*b* approach the vertical position, stent 10 slides downward along support portions 44*a* and 44*b* in the direction of arrow 56, as depicted in FIG. 5B, until arms 24*a* and 24*b* reach the vertical position depicted in FIG. 5C upon rotation one half-turn or 180°. Continued rotation of mandrel 22 allows stent 10 to move back and forth along support portions 44*a* and 44*b* between elbows 46*a* and 46*b* in the direction of double arrow 58 depicted in FIG. 5C. Such constant back and forth movement of stent 10 along support portions 44 upon rotation of mandrel 22 during the coating process allows the contact points between stent 10 and mounting assembly 18 to be transient rather than permanent, thereby preventing the coating material from flowing, wicking, collecting, and solidifying at or between arms 24 and stent 10. In some embodiments, the back and forth motion of stent 10 along arms 24 is enhanced by downward forces exerted throughout the coating process by atomization airflow during the spraying cycle and/or dryer airflow during the drying cycle.

Coating a Stent Using the Mounting Assembly

The following method of application is being provided by way of illustration and is not intended to limit the embodiments of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi, for example 15 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition. The solution barrel pressure can be between 1 to 3.5 psi, for example 2.5 psi. The temperature of the nozzle can adjusted to a temperature other than ambient temperature during the spray process by the use of a heating block or other similar devices. For example, the temperature of the nozzle can be between 45° to about 88°, the temperature depending on a variety of factors including the type and amount of polymer, solvent and drug used. The nozzle can be positioned at any suitable distance away form the stent, for example, about 10 mm to about 19 mm.

During the application of the composition, mandrel 22 can be rotated about its own central longitudinal axis. Rotation of mandrel 22 can be from about 10 rpm to about 300 rpm, more narrowly from about 40 rpm to about 240 rpm. By way of example, mandrel 22 can rotate at about 100 rpm. Mandrel 22 can also be moved in a linear direction along the same axis. Mandrel 22 can be moved at about 1 mm/second to about 6 mm/second, for example about 3 mm/second, or for at least two passes, for example (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/$cm^2$ (of stent surface) to about 40 micrograms/$cm^2$, for example less than about 2 micrograms/$cm^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 85° C., more narrowly from about 40° C. to about 55° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The blower pressure can be, for example between 10 to 35 psi, more narrowly 12 to 15 psi and can be positioned at a distance of about 10 to 20 mm away from the stent. The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single application can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55% the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, anti fibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for supporting a stent during a stent coating process, comprising:

positioning a stent on an apparatus comprising a first arm element for engagement with a first section of a stent and a second arm element for engagement with a second section of the stent, wherein at least one of the first and second arm elements can be pivoted from a first position to a second position so as to have a first angle between the first and second arm elements for supporting the stent and pivoted from the second position to the first position so as to have a second angle between the first and second arm elements for releasing of the stent, wherein at least one of the first and second arm elements are coupled to a mandrel, the mandrel configured to penetrate at least partially in a longitudinal bore of the stent; and applying a coating material to the stent.

2. The method of claim 1, wherein the first and second arm elements are coupled to a base member.

3. The method of claim 1, wherein the stent comprises frame elements and openings in the frame elements, and the first and second arm elements penetrate into the openings in the frame elements when the first and second arm elements engage the stent.

4. The method of claim 1, wherein the mandrel is positioned between the first and second arm elements, and wherein when the stent is in a support position, the first and second arm elements are in contact with the mandrel.

5. The method of claim 1, wherein the second angle is greater than the first angle.

6. A method for supporting a stent during a stent coating process, comprising:

positioning a stent on an apparatus comprising a first arm element for engagement with a first section of a stent, and a second arm element for engagement with a second section of the stent, wherein in a natural configuration, the arm elements are in an engaged configuration with the stent and wherein with an application of a force, the arm elements can be biased relative to each other for disengagement of the stent, wherein at least one of the first and second arm elements are coupled to a mandrel, the mandrel configured to penetrate at least partially in a longitudinal bore of the stent; and applying a coating material to the stent.

7. The method of claim 6, wherein the first and second arm elements are coupled to a base element.

8. The method of claim 6, wherein the stent comprises frame elements and openings in the frame elements, and the first and second arm elements penetrate into the openings of the frame elements when in the engaged configuration.

9. The method of claim 6, wherein the mandrel is positioned between the first and second arm elements, and wherein in the engaged configuration, the first and second arm elements contact the mandrel.

10. A method for supporting a stent during a coating process, comprising:

supporting the stent on a first member, a second member, and a third member, the second member capable of bending between a first position and a second position so as to allow the stent to be releasably supported by the first and second members, the third member capable of bending between a first position and second position to allow the stent to be releasably supported by the first, second and third members; and applying a coating material to the stent.

11. The method of claim 10, wherein the first member is capable of being inserted at least partially through a longitudinal bore of the stent.

12. The method of claim 10, wherein the first member is capable of bending between a first position and a second position.

13. The method of claim 10, wherein the first and second members extend from a base member.

14. The method of claim 10, wherein the second member makes contact with the first member when the stent is being supported by the device.

15. The method of claim 10, wherein the first member is configured to be disposed within a bore of the stent and the second member is configured to penetrate a gap between struts of the stent.

16. The method of claim 10, wherein the first member is capable of bending between a first position and a second position and wherein the first, second, and third members are configured to penetrate into lateral gaps between struts of the stent.

17. The method of claim 10, wherein the second member comprises a non-linear arm element.

18. The method of claim 10, wherein a length of the second member is shorter than a length of the first member.

19. A method for supporting a stent during a coating process, comprising:

positioning a stent on a first arm element extending from a base member and a second arm element extending from the base member, wherein the second arm element is adapted to be pressed into a depression in the base member, and when pressed into the depression the second arm element flexes from a first position to a second position, the first position for holding the stent on the first and second arm elements, the second position for releasing the stent from the first and second arm elements; and applying a coating material on the stent.

20. The method of claim 19, wherein the first arm element is adapted to be flexed from a first position to a second position so as to allow the stent to be releasably supported by the device.

21. The method of claim 20, wherein each of the first and second arm elements comprise a first section and a second section extending at an angle from the first section, such that the second sections are adapted to engage the stent.

22. The method of claim 21, wherein the stent does not make contact with the first sections when the stent is in a support position.

23. The method of claim 19, wherein when the stent is supported by the device, the stent does not make contact with the base member.

24. The method of claim 19, wherein the first arm element is adapted to be inserted into a longitudinal bore of the stent.

25. The method of claim 19, wherein the second arm element includes a first section and a second section extending at an angle from the first section, such that the second section is adapted to engage the stent.

26. The method of claim 25, wherein the stent does not make contact with the first section of the arm element when the stent is in a support position.

27. A method for supporting a stent during a stent coating process, comprising:

positioning a stent on a device comprising a first arm element for engagement with a first section of a stent and a second arm element for engagement with a second section of the stent, wherein the first or second arm elements is configured to be pivoted or bent from a first position to a second position for penetrating into a gap between a support structure of the stent and pivoted or bent from the second position to the first position for retracting out of the gap between the support structure of the stent, and wherein the first arm element comprises a mandrel for being disposed in a longitudinal bore of a stent and the second arm element is connected to the first arm element; and applying a coating composition to the stent.

28. The method of claim 27, wherein a base is coupled to the first and second arm elements.

29. A method for supporting a stent during a stent coating process, comprising:

positioning a stent on a device comprising a first member extending from a base and a second member extending form the base;

rotating the base, wherein during the rotation of the base, the stent moves back and forth relative to the first and second members; and applying a coating material to the stent wherein the first member is a mandrel member having a diameter smaller than the inner diameter of the stent as positioned on the device.

30. The method of claim 29, wherein the first member is configured to be inserted through a longitudinal opening at an end of the stent and into a longitudinal bore of the stent.

31. The method of claim 29, wherein the first and second members are clamp members for releaseably holding the stent.

32. The method of claim 19, wherein positioning the stent on the apparatus includes applying a force to the second arm element so that the second arm element flexes inside the depression.

33. The method of claim 19, wherein the first arm is adapted to be pressed into the depression in the base, and when pressed into the depression, the first arm flexes from a first position to a second position, the first position for holding the stent on the first and second arm elements, the second position for releasing the stent from the first and second arm elements.

34. A method of supporting a stent during a stent coating process comprising: positioning a stent on a device comprising: a first member extending from a base and a second member extending from the base; rotating the base, wherein during the rotation of the base, the stent moves back and forth relative to the first and second members; and applying a coating material to the stent, wherein the first member passes through a lateral gap between struts of the stent, wherein the second member passes through another lateral gap between the struts of the stent and the device further includes a third member extending from the base and passing through a longitudinal opening at an end of the stent.

* * * * *

UNITED STATES PATENT AND TRADEMARK OFFICE

CERTIFICATE OF CORRECTION

PATENT NO. : 7,648,725 B2
APPLICATION NO. : 11/437589
DATED : January 19, 2010
INVENTOR(S) : Van Sciver et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 851 days.

Signed and Sealed this

Twenty-eighth Day of December, 2010

David J. Kappos

*Director of the United States Patent and Trademark Office*